United States Patent [19]
Weiss et al.

[11] Patent Number: 6,143,293
[45] Date of Patent: Nov. 7, 2000

[54] ASSEMBLED SCAFFOLDS FOR THREE DIMENSIONAL CELL CULTURING AND TISSUE GENERATION

[75] Inventors: Lee E. Weiss; Jay Wynn Calvert, both of Pittsburgh, Pa.

[73] Assignees: Carnegie Mellon; University of Pittsburgh, both of Pittsburgh, Pa.

[21] Appl. No.: 09/048,944

[22] Filed: Mar. 26, 1998

[51] Int. Cl.[7] ............................ A61K 35/12; C12N 11/16; C12N 11/14; C12N 11/08; C12N 5/00

[52] U.S. Cl. .......................... 424/93.7; 424/423; 424/520; 435/174; 435/176; 435/177; 435/180; 435/395; 435/396; 435/401; 435/402

[58] Field of Search ..................... 435/174, 176, 435/177, 180, 182, 395, 396, 397, 398, 401, 402; 424/93.7, 423, 520

[56] References Cited

U.S. PATENT DOCUMENTS

| | | | |
|---|---|---|---|
| 4,235,246 | 11/1980 | Weiss | 607/131 |
| 4,299,239 | 11/1981 | Weiss et al. | 607/131 |
| 4,579,380 | 4/1986 | Zaremsky et al. | 294/119.1 |
| 4,902,295 | 2/1990 | Walthall et al. | 623/11 |
| 4,963,489 | 10/1990 | Naughton et al. | 435/1.1 |
| 4,970,298 | 11/1990 | Silver et al. | 530/356 |
| 4,997,443 | 3/1991 | Walthall et al. | 623/11 |
| 5,032,508 | 7/1991 | Naughton et al. | 435/32 |
| 5,041,138 | 8/1991 | Vacanti et al. | 623/16 |
| 5,079,974 | 1/1992 | Weiss et al. | 76/107.1 |
| 5,160,490 | 11/1992 | Naughton | 435/287.1 |
| 5,189,781 | 3/1993 | Weiss et al. | 29/527.2 |
| 5,266,476 | 11/1993 | Sussman et al. | 435/399 |
| 5,266,480 | 11/1993 | Naughton et al. | 435/371 |
| 5,286,573 | 2/1994 | Prinz et al. | 264/308 |
| 5,301,415 | 4/1994 | Prinz et al. | 29/458 |
| 5,301,863 | 4/1994 | Prinz et al. | 228/33 |
| 5,308,764 | 5/1994 | Goodwin et al. | 435/1.1 |
| 5,312,456 | 5/1994 | Reed et al. | 411/454 |
| 5,399,665 | 3/1995 | Barrera et al. | 528/354 |
| 5,410,016 | 4/1995 | Hubbell et al. | 528/354 |
| 5,443,950 | 8/1995 | Naughton et al. | 435/1.1 |
| 5,478,739 | 12/1995 | Slivka et al. | 435/399 |
| 5,496,722 | 3/1996 | Goodwin et al. | 435/371 |
| 5,510,254 | 4/1996 | Naughton et al. | 435/370 |
| 5,512,475 | 4/1996 | Naughton et al. | 424/484 |
| 5,516,680 | 5/1996 | Naughton et al. | 435/369 |
| 5,516,681 | 5/1996 | Naughton et al. | 435/353 |
| 5,518,915 | 5/1996 | Naughton et al. | 424/422 |
| 5,541,107 | 7/1996 | Naughton et al. | 435/29 |
| 5,567,435 | 10/1996 | Hubbell et al. | 424/426 |
| 5,567,612 | 10/1996 | Vacanti et al. | 435/366 |
| 5,569,272 | 10/1996 | Reed et al. | 606/151 |
| 5,578,485 | 11/1996 | Naughton et al. | 435/32 |
| 5,580,781 | 12/1996 | Naughton et al. | 435/1.1 |
| 5,618,718 | 4/1997 | Auger et al. | 435/366 |
| 5,624,840 | 4/1997 | Naughton et al. | 435/395 |
| 5,626,863 | 5/1997 | Hubbell et al. | 424/426 |
| 5,674,848 | 10/1997 | Bhatnagar | 514/14 |
| 5,676,850 | 10/1997 | Reed et al. | 216/2 |
| 5,770,417 | 6/1998 | Vacanti et al. | 435/180 |

FOREIGN PATENT DOCUMENTS

| | | |
|---|---|---|
| WO88/03785 | 6/1988 | WIPO. |
| WO93/19700 | 10/1993 | WIPO. |
| WO96/03094 | 2/1996 | WIPO. |
| WO96/40002 | 12/1996 | WIPO. |
| WO97/39624 | 10/1997 | WIPO. |

OTHER PUBLICATIONS

Antonios G. Mikos et al, Laminated three–dimensional biodegradable foams for use in tissue engineering, Biomaterials, 1993, 323–30, vol. 14, Butterworth–Heinemann Ltd., USA.

Robert Langer et al, Tissue Engineering, Science, May 14, 1993, 920–25, vol. 260.

Friedrich B. Prinz et al, JTEC/WTEC Panel Report on Rapid Prototyping in Europe and Japan, Rapid Prototyping Association of the Society of Manufacturing Engineers, Mar. 1997, 5–19, Rapid Prototyping Association of the Society of Manufacturing Engineers.

Robert J. Klebe, Cytoscribing: A Method of Micropositioning Cells and the Construction of Two–and Three–Dimensional Synthetic Tissues, Experimental Cell Research, 1988, 362–73, vol. 179, Academic Press.

L. E. Weiss et al, Shape Deposition Manufacturing of Heterogenous Structures, Journal of Manufacturing Systems, 1997, 239–248, vol. 16/No. 4.

Lichun Lu et al, The Importance of New Processing Techniques in Tissue Engineering, MRS Bulletin, Nov. 1996, 28–32.

Robert Langer et al, Artificial Organs, Scientific American, Sep. 1995, 130–133.

Steven Ashley, Rapid Prototyping for Aritficial Body Parts, Mechanical Engineering, May 1993, 50–53.

Viljanen, et al. Comparison of the Tissue Response to Absorbable Self–Reinforced Polylactide Screws and Metallic Screws in the Fixation of Cancellous Bone Osteotomies: An Experimental Study on the Rabbit Distal Femur, J. Orthopaedic Reserach, p. 398–407 (1997).

Nicaeus, et al, Sucralfate and Basic Fibrolast Growth Factor Promote Endothelial Cell Proliferation Around Porous Alloplastic Implants In Vitro, p. 235–239 (1996).

Takahisa Okano, et al., Hybrid Muscular Tissues: Preparation of Skeletal Muscel Cell–Incorporated Collagen Gels, Cell Transplantation 109–118 (1997).

Lee, Goonhee et al., Selective Laser Sintering of Bioceramic Materials for Implanting, Solid Freeform Fabrication Symposium University of Texas at Austin, 1993.

Weiss, L. et al., Shape Deposition Manufacturing of Wearable Computers, Solid Freeform Fabrication Symposium University of Texas at Austin, 1996.

Kim, Enoch et al., Making Polymeric Microstructures: Capillary Micromolding, Technical Note, 1997.

Lee, Goonhee et al., Selective Laser Sintering of Calcium Phosphate Powders, Solid Freeform Fabrication Symposium University of Texas at Austin, 1994.

Bourell, D.L. et al., Solid Freeform Fabrication and Advanced Manufacturing Approach, Solid Freeform Fabrication Symposium University of Texas at Austin, 1990.

Xia, Younan, et al., Soft Lithography, 1997.

*Primary Examiner*—David M. Naff
*Attorney, Agent, or Firm*—Raymond A. Miller; Reed Smith Shaw & McClay LLP

[57] ABSTRACT

A three-dimensional scaffold for tissue generation. Mechanical fasteners allow layered and volumetric scaffold sections, which may be pre-seeded with cells and/or growth factors, to be assembled into a heterogeneous generated tissue for implantation.

19 Claims, 10 Drawing Sheets

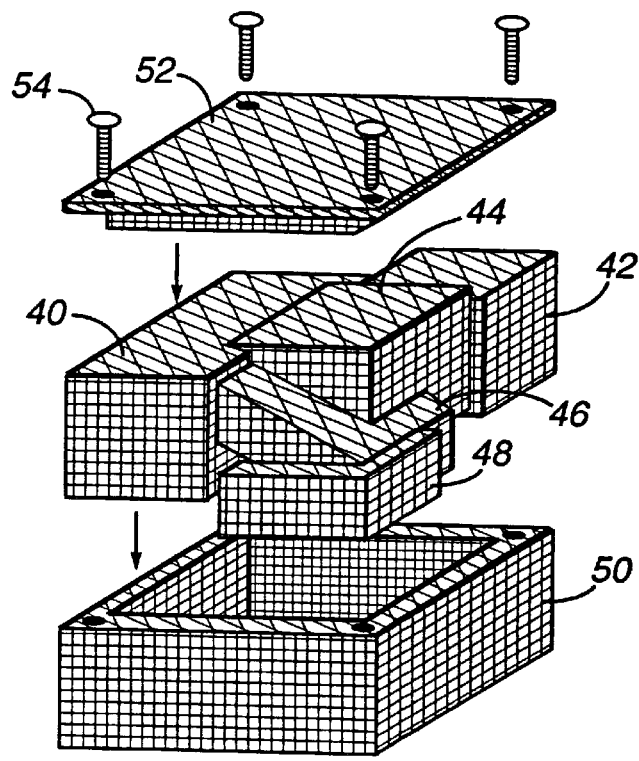
FIGURE 17
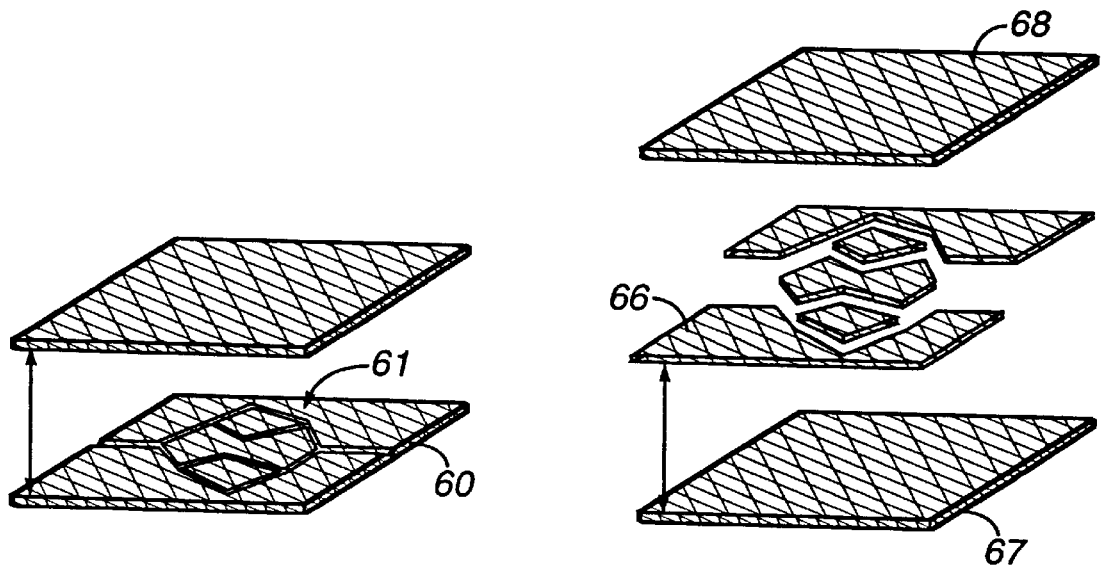
FIGURE 18   FIGURE 19

ASSEMBLED SCAFFOLDS FOR THREE DIMENSIONAL CELL CULTURING AND TISSUE GENERATION

FIELD OF THE INVENTION

The present invention relates to apparatus and techniques for performing tissue generation. In particular, the invention relates to scaffolds which may be prepared in three dimensions in order to support 3-dimensional cell cultures and promote guided tissue generation. The scaffold is preferably, but need not be, bio-absorbable.

BACKGROUND OF THE INVENTION

Tissue engineers seek to repair, replace, or regenerate damaged or diseased tissues by manipulating cells, creating artificial implants, or synthesizing laboratory-grown substitutes. One regenerative tissue engineering approach involves a process known as "tissue induction," whereby 2½ and 3-dimensional polymer or mineral scaffolds without cells are implanted in a patient. With tissue induction, tissue generation occurs through ingrowth of surrounding tissue into the scaffold.

Another approach to tissue generation, known as "cell transplantation," involves seeding scaffolds with cells, cytokines, and other growth-related molecules, then culturing and implanting these constructs to induce the growth of new tissue. Cultured cells are infused in a biodegradable or non-biodegradable scaffold, which may be implanted directly in the patient, or may be placed in a bioreactor (in-vitro) to allow the cells to proliferate before the tissue is implanted in the patient. Alternatively, the cell-seeded scaffold may be directly implanted, in which case the patient's body acts as an in-vivo bioreactor. Once implanted, in-vivo cellular proliferation and, in the case of absorbable scaffolds, concomitant bio-absorption of the scaffold, proceeds.

In both types of tissue engineering, i.e., tissue induction and cell transplantation, the scaffold, whether or not bioabsorbable, must be biocompatible, such that it does not invoke an adverse immune response from, or result in toxicity to, the patient.

There exist numerous techniques for manufacturing scaffolds for tissue generation.

The techniques used are often dictated by the type of tissue ultimately being generated. One approach involves machining coraline hydroxyapatite to a desired shape. Another technique, known as "fiber bonding", involves preparing a mold in the shape of the desired scaffold and placing fibers, such as polyglycolic acid (PGA) into the mold and embedding the PGA fibers in a poly (L-lactic acid) (PLLA)/methylene chloride solution. The solvent is evaporated, and the PLLA-PGA composite is heated above the melting temperatures of both polymers. The PLLA is then removed by selective dissolution after cooling, leaving the PGA fibers physically joined at their cross-points without any surface or bulk of modifications and maintaining their initial diameter. Fiber bonding is useful for fabrication of thin scaffolds.

Another technique for manufacturing scaffolds is known as "solvent-casting and particulate-leaching." In this technique, sieved salt particles, such as sodium chloride crystals, are disbursed in a PLLA/chloroform solution which is then used to cast a membrane. After evaporating the solvent, the PLLA/salt composite membranes are heated above the PLLA melting temperature and then quenched or annealed by cooling at controlled rates to yield amorphous or semi-crystalline forms with regulated crystallinity. The salt particles are eventually leached out by selective dissolution to produce a porous polymer matrix.

Yet another technique used for constructing three-dimensional scaffolds is known as "melt molding", wherein a mixture of fine PLGA powder and gelatin microspheres is loaded in a Teflon® mold and heated above the glass-transition temperature of the polymer. The PLGA-gelatin composite is removed from the mold and gelatin microspheres are leached out by selective dissolution in distilled de-ionized water. Other scaffold manufacturing techniques include polymer/ceramic fiber composite foam processing, phase separation, and high-pressure processing.

Whichever type of scaffold is selected, the scaffold's purpose is to support cells, which, after being seeded into the scaffold, cling to the interstices of the scaffold and replicate, produce their own extra-cellular matrices, and organize into the target tissue.

Many of the above-described techniques require the use of severe heat or chemical treatment steps, which preclude seeding cells into the scaffold while it is being built, rather, require waiting until the entire scaffold has been constructed. This presents a challenge to seeding cells in three-dimensional scaffolds. None of the known scaffold materials allow growth of cells to a depth of greater than about 250 micrometers, which is a generally accepted practical limit on the depth to which cells and nutrients can diffuse into scaffolds having the desired porosities. Even if cells could be made to diffuse to greater depths, it is generally believed that to support cell growth and avoid or at least curtail apoptosis at these depths, the scaffold must also support some form of vasculature to promote angiogenesis; none of the scaffold fabrication techniques just discussed, however, allow for incorporation of blood vessels.

The cell transplantation approach has been used to produce bone, cartilage, liver, muscle, vessels, and skin analogues. In this approach, depicted in FIG. 1, cultured cells 100 are seeded into a three-dimensional, biodegradable scaffold 102. The resulting cellular construct, 104, is either cultured in-vivo, in a bioreactor 106, such as a broth medium placed in an incubator prior to implantation, 108, or is directly implanted in an animal or the patient 110. These synthesized tissues, however, replicate the histological composition and function of the desired tissue with varying degrees of accuracy. Complete organs, such as livers, and entire functioning groups, such as a vascularized bone with attached tendon and muscle, have yet to be demonstrated. These limitations are due, in part, to restrictions of the manufacturing methods presently used to fabricate three dimensional scaffolds, discussed above, which limit scaffold constructs to be homogeneous in microstructure, material composition, cell type and distribution.

Furthermore, except for monolayer structures, scaffolds have not been successfully developed for supporting heterogeneous selective cell seeding within the same scaffold.

Rather, current approaches use one type of scaffold material to promote one type of cell growth. For example, in the case of bone regeneration, optimal pore size for maximum tissue growth ranges from 200–400 μm, and so scaffold materials with this pore size and having sufficient rigidity and biochemical properties to support loads are used for generating bone tissue. There exist, however, very few biological tissues, with skin and cartilage being possible exceptions, that can be accurately fabricated using only one type of cell supported on one type of scaffold. Most tissues are made up of numerous different cell types, each of which requires a different scaffold, possibly different growth factors, as well as different blood vessel architecture to ensure viability. For example, a limb is comprised of bone, muscle and tendon. Scaffolds such as hydroxyapatite, useful to support bone cells, are too brittle and non-pliable to act as scaffolding for muscle or tendons. Other heterogeneous tissues, such as liver and kidney, are even more complex. Most current scaffolds and tissue engineering techniques fail to permit heterogeneous tissues to be grown or provided with blood vessels. Furthermore, it has been suggested that cell growth factors should be present in concentration gradients in order to maximize cell development. Most current scaffold fabrication methods have no direct means of directly creating controlled gradients of growth factor, with the possible exception of 3-D printing.

The capability to create heterogeneous scaffold seeding systems would help to enable the regeneration of tissues, and collections of tissues, which exhibit more accurate histological structure and function than can be achieved with homogeneous constructs alone. This capability would permit different cells to be strategically placed in different regions of the scaffold, and each region could be composed of the optimal scaffold material and microstructure for organizing and stimulating the growth of cells in that region.

As is now apparent, one of the problems encountered by the tissue engineer is the need to incrementally build up scaffold material, selectively implant cells and growth factors throughout the entire scaffold and embed a vascular supply. A process known as solid freeform fabrication may offer some solutions. Solid freeform fabrication (SFF) refers to computer-aided-design and computer-aided-manufacturing (CAD/CAM) methodologies which have been used in industrial applications to quickly and automatically fabricate arbitrarily complex shapes. SFF approaches to creating scaffolds for tissue engineering are also being investigated.

SFF processes construct shapes by incremental material buildup and fusion of cross-sectional layers. In these approaches, illustrated in FIG. 2, a three-dimensional (3D) CAD model 112 is first decomposed, or "sliced", via an automatic process planner 114, into thin cross-sectional layer representations which are typically 0.004 to 0.020 inches thick. To build the physical shape, each layer is then selectively added or deposited and fused to the previous layer in an automated fabrication machine 116.

Rapid prototyping of design models, as discussed in Prinz, JTEC/WTEC Panel Report on Rapid prototyping in Europe and Japan (March 1997) incorporated in its entirety by reference herein, has proven useful for industrial applications. In such an approach, in order to support the structure as it is being built up, sacrificial layers may also be deposited when required, as illustrated in FIGS. 3 and 4. In one approach, each physical layer 118, which consists of the cross-section and a complementary shaped sacrificial layer, is deposited and fused to the previous layer as illustrated in FIG. 3, using one of several available deposition and fusion technologies. The sacrificial material 120 has two primary roles. First, it holds the part, analogous to a fixture in traditional fabrication techniques. Second, it serves as a substrate upon which "unconnected regions" 122 and overhanging features 124 can be deposited. The unconnected regions require this support since they are not joined with the main body until subsequent layers are deposited. Another use of sacrificial material is to form blind cavities 126 in the part. The sacrificial material is removed when the part is completely built up. As illustrated in FIG. 4, other building approaches only use support structures 128 where required, i.e., for the unconnected regions and steep overhanging features. These explicit support structures are typically deposited with the same material as the object being formed, but are drawn out in a semisolid fashion so that it is easy to remove these supports when the part is completed. For example, they may be deposited as thin wall structures.

There are several deposition and fusion processes currently in use or being developed for SFF. Some representative examples of SFF processes, which have also been investigated for tissue engineering applications, are illustrated in FIGS. 5 and 6. In the selective laser sintering process, depicted in FIG. 5, a layer of powdered material 130 is spread over the top surface of the growing structure 131. A $CO_2$ laser 132 is then used to selectively scan the layer to fuse those areas defined by the geometry of the cross-section; this also fuses subsequent layers together. The laser beam is directed using computer-controlled mirrors 134 directed by the CAD data. The unfused material 136 remains in place as the support structure. After each layer is deposited, an elevator platform 138 lowers the part 131 by the thickness of the layer and the next layer of powder is deposited. When the shape is completely built up, the part is separated from the loose supporting powder. Subsequent heat treatment might also be required. Several types of materials have been investigated, including metals, ceramics, polymers, and polymer-coated metals and ceramics. While the materials which have been identified are primarily for industrial applications, the fabrication of hydroxyapatite scaffolds using selective laser sintering have been investigated using polymer-coated calcium phosphate powder. Additional post-processing, such as high temperature heating which burns out the binder, and then higher temperature sintering which fuses the powder together, is required to strengthen the part.

The three-dimensional printing (3D printing) process, depicted in FIG. 6, is another powder-based SFF approach used in industrial applications, but with potential use in forming scaffolds for engineered tissue. An ink-jet printing mechanism 140 scans the powder surface 142 and selectively injects a binder into the powder, which joins the powder together, into those areas defined by the geometry of the cross-section. As with selective laser sintering, an elevator platform 144 lowers the part 141 by the thickness of the layer and the next layer of powder is applied by the ink jet. When the shape 141 is completely built up, the part is separated from the loose supporting powder. The use of 3D printing for fabricating biomaterial structures out of bovine bone and biopolymers have also been used. The potential of 3D printing to intimately control the orientation and placement of porous channels and the overall shape of a device could make 3D printing well-suited for producing tissue generation devices. For example, microchannels to help support angiogenesis can be created in the scaffold using this technique. It would also be feasible to use the same or different microchannels to support cell growth via infused cells, harvest medium, growth factors, blood, etc. However, since the feature size achievable with 3D printing is about 100 $\mu$m, a modified building strategy is required to fabricate highly porous, small diameter microstructures. To make porous polymer scaffolds, salt is used as the powder and the polymer is used as the binder. The salt, which acts as a porogen, is leached out of the completed shape by dissolving the completed shape in water, leaving a porous polymer scaffold.

"Membrane lamination" is another SFF-like technique used for constructing three-dimensional biodegradable polymeric foam scaffolds with precise anatomical shapes. First, a contour plot of the particular three-dimensional shape is prepared. Highly porous PLLA or PLGA membranes having the shapes of the contour are then manufactured using the solvent-casting and particulate-leaching technique. Adjacent membranes are bonded together by coating chloroform on their contacting surfaces. The final scaffold is thus formed by laminating the constituent membranes in the proper order to create the desired three-dimensional shape.

In addition to the capability to build up complex shapes, fabricating shapes by incremental material addition techniques allows multi-material structures to be created, by using selective deposition techniques, and prefabricated components to be embedded within the structures as they are being built up. For example, FIG. 7 depicts such a heterogeneous structure 150, with embedded components 152, multi-materials 154, and support materials 156. Such structures have been created for industrial applications, with a process called Shape Deposition Manufacturing (SDM).

As discussed previously, scaffold fabrication methods, whether conventional, SFF or SDM, typically involve heat or chemical actions which would destroy living cells or compromise the growth factors. With these methods, cells can only be added to the scaffolds after they have been prefabricated. Growth factors can also be added at or prior to this point. For a discussion of incorporating growth factors into scaffold materials, see Saltsman, "Growth-Factor Delivery in Tissue Engineering," MRS Bulletin, Nov. 1996, p. 62–65. Completed scaffolds are impregnated with cells by exposing them to cells suspended in liquid culture media; the cells then diffuse into and attach to the scaffolds. Assuming that the cells are given enough time to diffuse into and throughout the scaffolds, then there will be a uniform distribution of cells; selective placement of cells in three dimensional scaffolds, once formed, is not feasible. Diffusion rates also limit the practical size (thickness) of scaffolds, as most cells and associated nutrients cannot diffuse to a depth of greater than about 250 microns into the scaffold. Even if cells could diffuse to greater depths, the scaffold would require blood vessels to support the deeply seeded cells. In addition, the fabrication techniques discussed tend to produce scaffolds with uniform microstructure. And, while scaffolds can be composites of different materials, the composition, including growth factors, is uniform throughout.

There are exceptions to some of the specific limitations just cited. For example, some cell culture and transplantation techniques incorporate cells directly in collagen matrices before the collagen is molded into the final scaffold shape. Further, 3D printing techniques can create nonhomogeneous microstructure. One approach suggested for preparing three-dimensional synthetic tissues is described in Klebe, "Cytoscribing: A Method for Micropositioning Cells and the Construction of Two- and Three-Dimensional Synthetic Tissues," Experimental Cell Research 179 (1988) pp. 362–373. Klebe discusses the use of ink jet printing techniques to selectively deposit cell adhesion proteins on a substrate. This technique uses monolayers of cells growing on thin sheets of collagen. The sheets can be attached to one another by gluing them together with collagen.

Still, while all of the existing scaffold fabrication methods can be useful techniques for specific applications, a general method for creating large scale, heterogeneous three dimensional scaffold systems, capable of supporting 3-dimensional cell culture and vascularization does not exist.

Accordingly, a significant advance in the art could be realized by a three-dimensional cellular scaffold that avoids one or more of the aforementioned shortcomings of the prior art.

SUMMARY OF THE INVENTION

According to the present invention, a three-dimensional scaffold is achieved by using mechanical fasteners, such as screws, sutures, and microbarbs in order to assemble layers and/or sections of scaffold material. In a preferred embodiment, cells have already been incorporated into each subsection of the scaffold prior to assembly.

In another preferred embodiment of the invention, different scaffold structures, for example, those having different porosities for supporting differentiated cells, are provided. The mechanical assembly techniques of the present invention allow for both different types of cells to be seeded, as well as for different types of scaffolds to be used to fabricate heterogeneous generated tissue.

To help address the challenge of manufacturing heterogeneous scaffolds, the present invention provides a method to build up scaffold constructs by mechanical assembly of individual layer or volume elements. These individual elements can be prefabricated using existing scaffold manufacturing processes such as solvent casting, shaping sections with machining, 3D printing, or molded collagen/cell constructs. These sections can then be mechanically mated using biodegradable or non-biodegradable barbs, pins, screws, clamps, staples, wires, string, or sutures. With this mechanical assembly approach, each prefabricated section can first be seeded with cells before assembly, and different scaffold materials, scaffold microstructure, and different cells can be placed in different sections of the scaffold. In addition, surface features on each scaffold subsection, which are readily fabricated, become part of the internal microstructure (e.g., molded surface channels become conduits for cell infusion, or for blood flow to stimulate angiogenesis). Furthermore, prefabricated vessel constructs can be embedded and assembled into the scaffold as it is being built up. The proposed methodology is based, in part, on the solid freeform fabrication (SFF) manufacturing paradigm, described herein.

According to the preferred embodiment, scaffolds are manufactured by mechanically assembling individual prefabricated layers (or, in general, volumetric elements) of scaffolding with fasteners. The prefabricated sections can first be manufactured using techniques such as those just described, including solvent casting, fiber bonding, melt molding, 3D printing, SFF, machining hydroxyapatite (HA), and molding collagen. In a preferred embodiment, following preparation of the individual sections of the scaffold, each prefabricated section is seeded with cells, before final assembly. In this way, cell viability is not compromised, as destructive heat or chemicals are not involved in the scaffold assembly process.

In another preferred embodiment of the invention, different materials, microstructure, and cells are used for making different sections of the scaffold.

These and other aspects of the preferred embodiment will become more readily apparent as the following detailed description of the invention proceeds, particularly when read in conjunction with the figures appended hereto.

FIGURES

The following is a brief description of the figures, presented for illustrative purposes to demonstrate the preferred embodiment in which:

FIG. 17 is a schematic representation of three dimensional scaffold sections being assembled in biodegradable containers according to the present invention.

FIGS. 18 and 19 are schematic representations of scaffold systems incorporating channels for angiogenesis according to the present invention.

DETAILED DESCRIPTION OF THE PREFERRED EMBODIMENT

Figure 1:
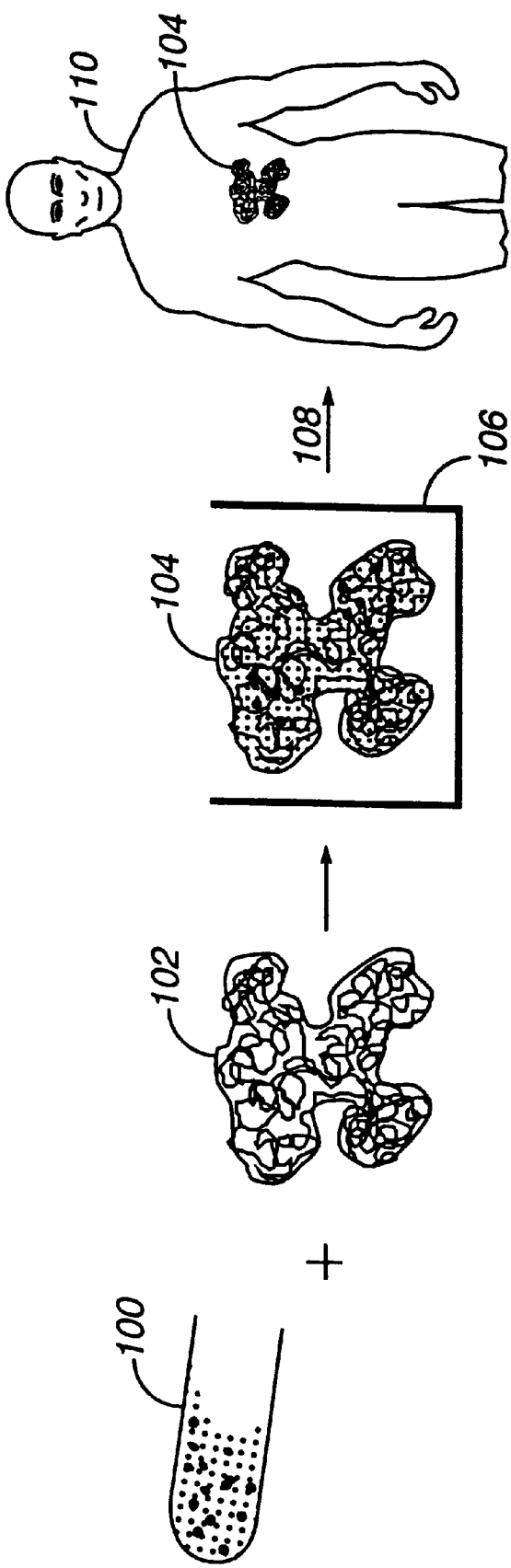
FIG. 1 is a schematic representation of three dimensional tissue culturing and cell transplantation.
Figure 2:
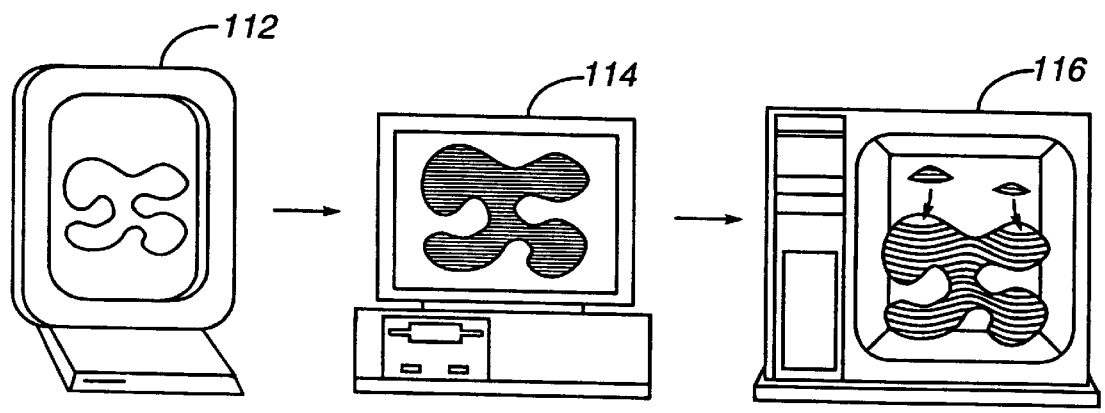
FIG. 2 is a schematic representation of a solid freeform fabrication technique.
Figures 3, 4:
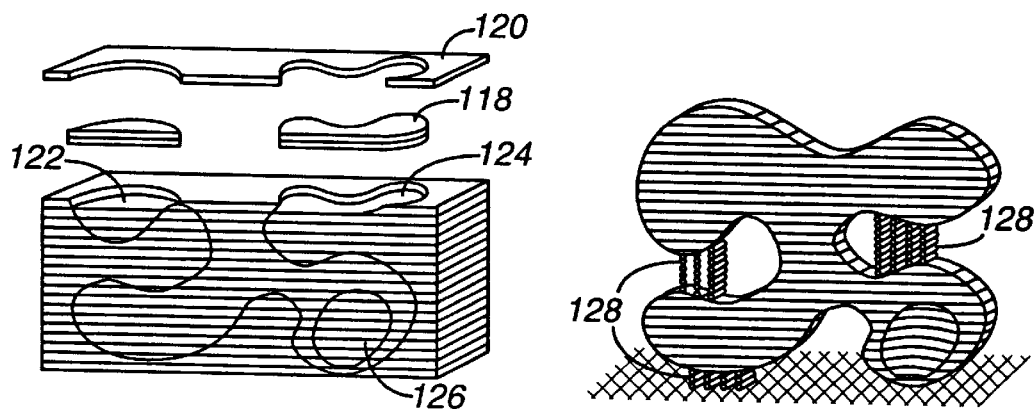
FIG. 3 is a schematic representation of complementary support structures for freeform fabrication.
FIG. 4 is a schematic representation of explicit support structures for freeform fabrication.
Figure 5:
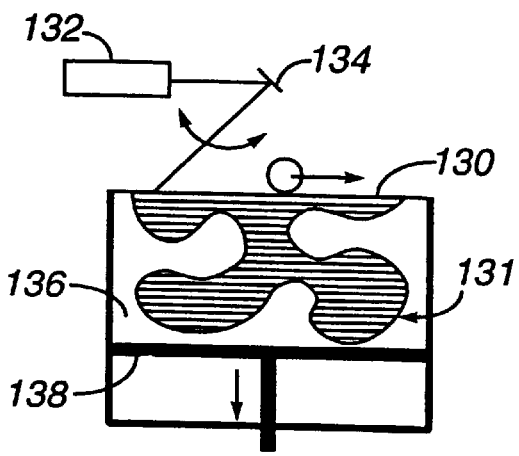
FIG. 5 is a schematic representation of a selective laser sintering freeform fabrication processes.
Figure 6:
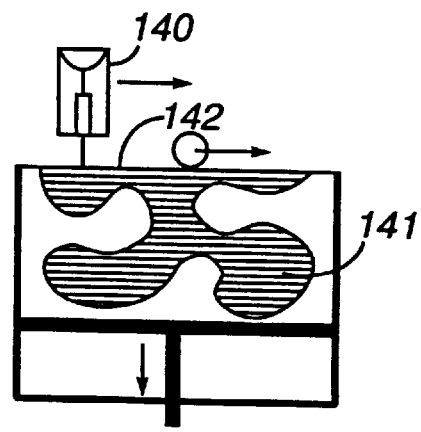
FIG. 6 is a schematic representation of a 3D printing freeform fabrication process.
Figure 7:
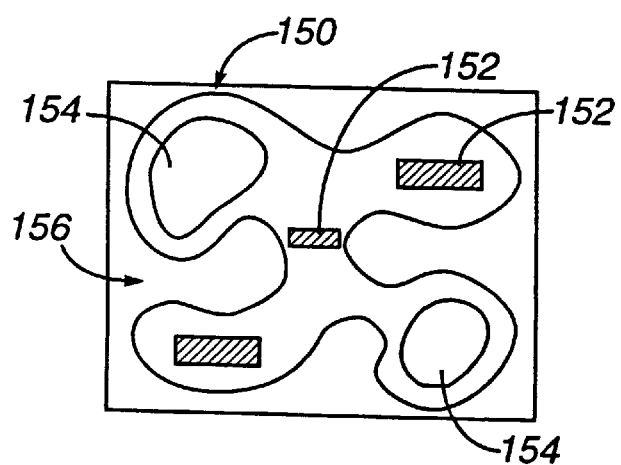
FIG. 7 is a schematic representation of a heterogeneous structure.
Figure 8:
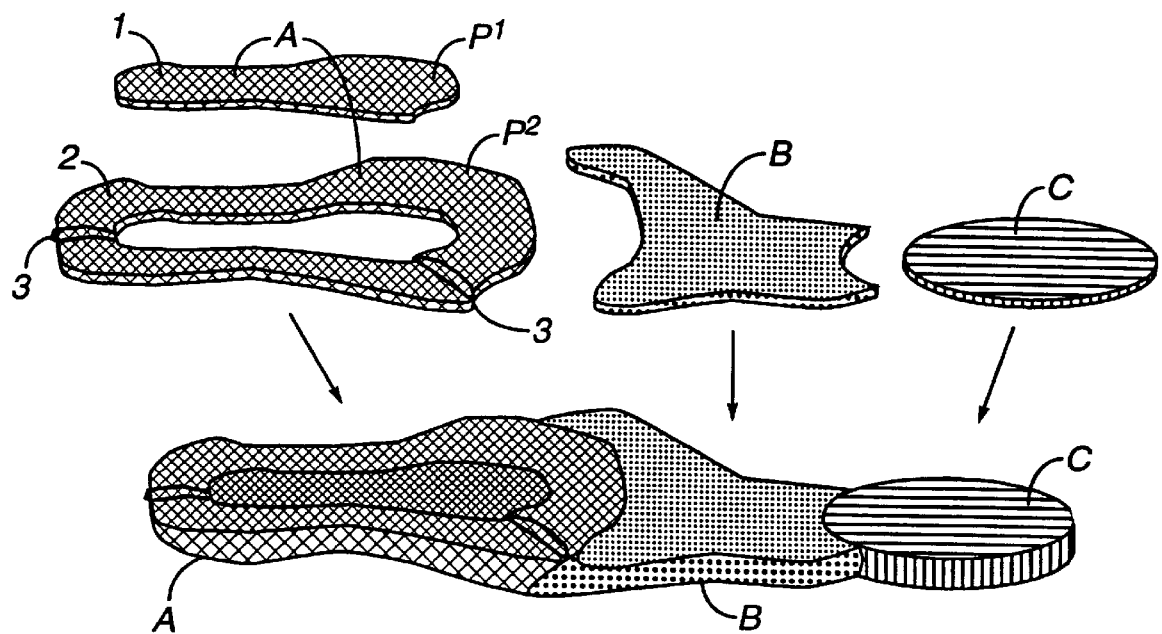
FIG. 8 is an exploded isometric view of a heterogeneous scaffold system of the present invention.

Referring to FIG. 8, there is illustrated a partially assembled heterogeneous construct of the invention, wherein a multiple-sectioned scaffold includes a subsection of scaffold for supporting bone cell growth A, a subsection for supporting tendon cell growth B, and a subsection for supporting muscle growth C. In this composite, each section, and even different layers within a section, can be made up of different materials and cells (e.g., osteoblasts or mesenchymal stem cells impregnated into machined hydroxyapatite for the bone sections A, satellite cells molded into collagen for the muscle sections C, and fibroblasts impregnated into yet another type of scaffold for tendon sections B). Individual segments 1 and 2 within a section can be manufactured with different porosities (P), as illustrated by porosities $P_1$ and $P_2$ for section A. Conduits 3 for embedding blood vessels and/or infusing cells can be molded into the surfaces of selected layers as illustrated. The subsections A, B and C are preferably first seeded with cells and then the subsections are joined together prior to implantation, using fasteners according to the present invention. Each subsection A, B and/or C could also have growth factors, different concentrations of growth factors, and different growth factors.

Figure 9:
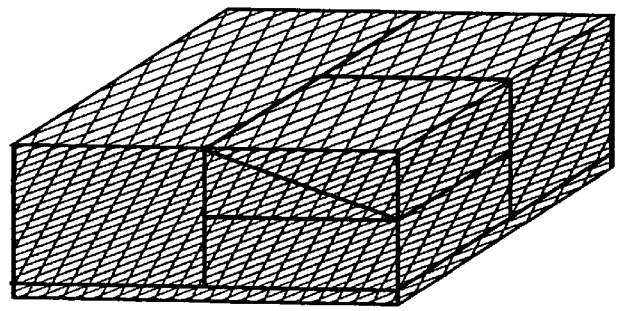
FIG. 9 is a schematic representation of a scaffold of the present invention composed of 3D subsections.

A preferred embodiment of the present invention uses seeded scaffolds mechanically fixed in close proximity in-vivo (or in a suitable bioreactor). The prefabricated elements need not be 2½ D structures (i.e., thin, three-dimensional shapes of uniform thickness). Most SFF processes have used 2½ D layers for two reasons: it is geometrically straight forward to decompose arbitrarily complex CAD models into layers, and the deposition and fusion processes which they use lend themselves to layering. In general, however, scaffold shapes for the present invention can be built up with three-dimensional volumetric elements of varying sizes and shapes, as illustrated in FIG. 9. As used herein, the term "three-dimensional" also includes planer structures of uniform thickness, but further includes non-planar three-dimensional structures and planar structures of non-uniform thickness, i.e., any structure with three dimensions. The surfaces of the volume elements need not be planar as depicted in FIG. 9; they could, for example, be curved surfaces.

According to the present invention, there are several methods by which scaffold sections can be mechanically assembled, preferably with biodegradable fasteners. The fasteners, fabricated, for example, from PLA/PGA, PEO, or polycarbonate, can be molded or machined. These fasteners, which can be used independently or in combination, include (but are not limited to), microbarbs, screws, sutures, pins, staples, wires, strings, and containers.

Figures 10, 11, 12:
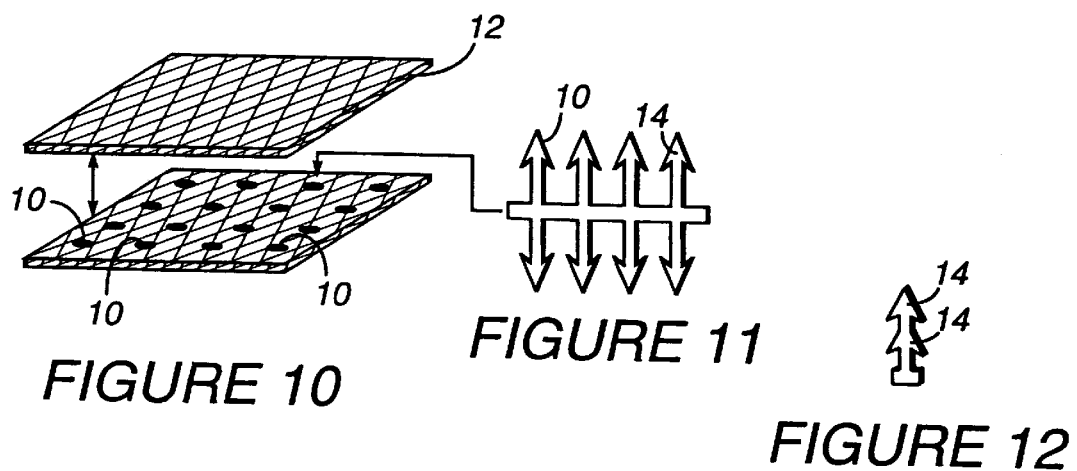
FIG. 10 is a schematic representation of 3D scaffolds assembled according to the present invention using microbarbs.
FIG. 11 is a schematic representation of a double-sided, single-hooked microbarb array useful in practicing the present invention.
FIG. 12 is a schematic representation of a double-hooked barb useful in practicing the present invention.

As illustrated in FIG. 10, microbarbs 10 can be positioned at intervals and used to penetrate and lock into porous scaffold materials 12. Polymer barbs can be fabricated using micromolding techniques such as described by Whitesides in "Making Polymeric Microstructures: Capillary Micromolding," technical note available from Department of Chemistry, Harvard University, Cambridge, Mass. 02138, incorporated in its entirety by reference herein. The scale of the barbs is preferably from about 25 $\mu$m to 250 $\mu$m or greater in height, depending upon the dimensions of the scaffold's porous microstructure. Each barb can have single (FIG. 11) or multiple (FIG. 12) hooks 14. Barbs can be used to mate with not only rigid or stiff scaffold materials, but also with compliant or elastic sections such as collagen. Another use of these barbs is to mate scaffolds to existing tissues in-vivo.

Another preferred embodiment uses double-sided barb arrays (FIG. 11) such that one side is first attached to one section of scaffold, then the second scaffold section is pressed onto the first section. As illustrated in FIG. 10, several barb fasteners 10 can be placed throughout the entire surface of a scaffold section to distribute the loads. Another approach is to use single-sided barb arrays, and attach the flat side to the first scaffold section with solvent (before seeding the first side with cells). Various combinations, including single-sided, single barbed, double-sided, double-barbed, or multiple barbs (in excess of two) can also be used.

Figures 13, 14:
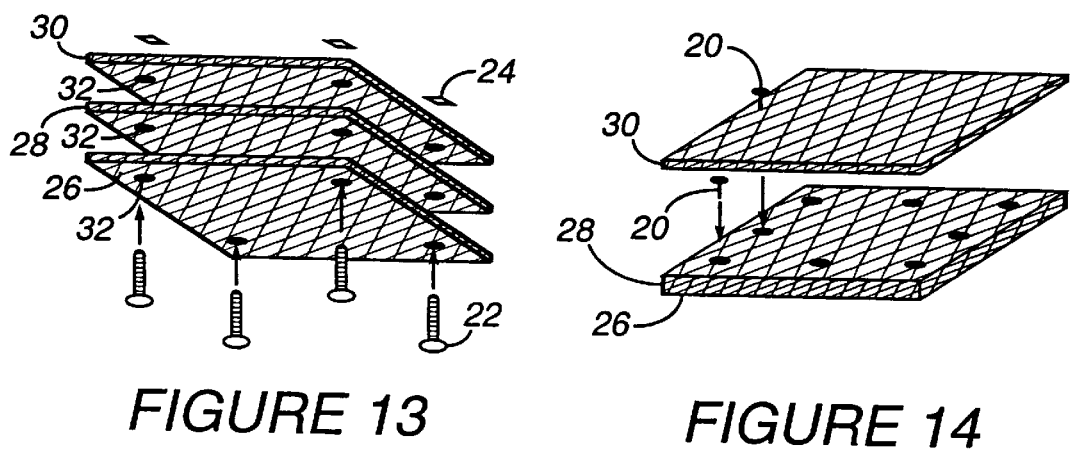
FIG. 13 is a schematic representation of multiple scaffold layers assembled with screws and nuts according to the present invention.
FIG. 14 is a schematic representation of assembling multiple layers of scaffold with miniature self-tapping screws according to the present invention.

In another preferred embodiment of the invention, illustrated in FIGS. 13 and 14, scaffold sections 26, 28, and 30 are screwed together with self-tapping screws 20, (FIG. 14) or with screw and nut combinations 22, 24 (FIG. 13). In one strategy, depicted in FIG. 13, screws 22 are first inserted up through predrilled holes 32 in the lower scaffold section 26, then the screw heads are bonded to the scaffold with solvents such as chloroform (before the lower section 26 is seeded with cells). Subsequent layers 28, 30, also with predrilled holes 32, are then stacked onto the lower section 26 and firmly assembled with nuts 24. Another preferred embodiment uses miniature self-taping screws 20 on a layer-by-layer basis as illustrated in FIG. 14. Screws are advantageously used when the scaffold is fabricated of a rigid or semi-rigid material, such as hydroxyapatite. For a discussion of the fabrication and use of bio-absorbable screws, see Viljanen, Pihlajamäki, Törmälä and Rokkanen, "Comparison of the Tissue Response to Absorbable Self-Reinforced Polylactide Screws and Metallic Screws in the Fixation of Cancellous Bone Osteotomies: An Experimental Study of the Rabbit Distal Femur," Journal of Orthopedic Research, Vol. 15 No. 3 p. 398–407 (1997).

Figure 15:
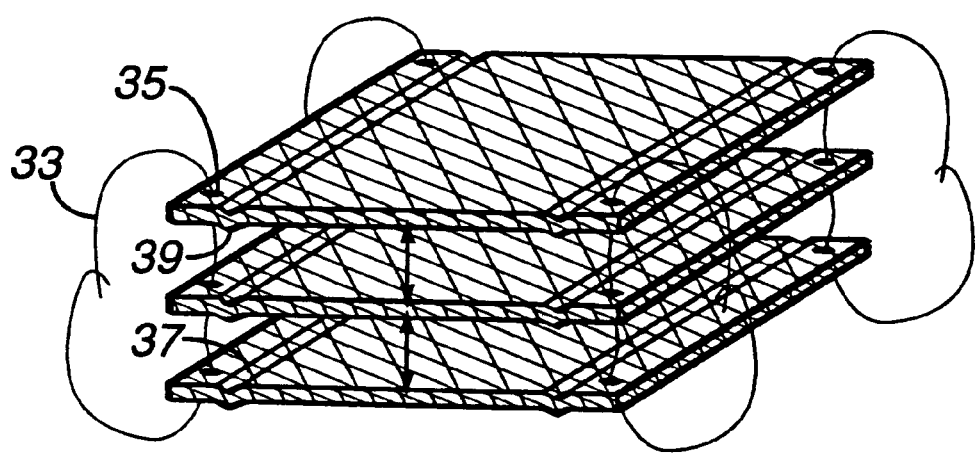
FIG. 15 is a schematic representation of multiple layers of scaffold being assembled with sutures according to the present invention.

In another preferred embodiment of the invention, illustrated in FIG. 15, scaffold layers or sections are fastened together using sutures, 33, which may be threaded through pre-existing holes 35, or sewn through unperforated sections of the scaffold layers. Since non-rigid sutures do not provide for accurate alignment between the sections, alignment can be provided using matched pairs of indentations or grooves 37 and mating protrusions 39 which can be easily molded into the scaffold sections. Sutures 33 are especially useful for fastening thin and/or pliable sections of scaffold material together. In a modified version of this embodiment, thin layers of scaffold sections, e.g., 1 mm thick hydroxyapatite, may be threaded onto a single suture, wire, or string, and suspended in a bioreactor with weights or clamping devices used to hold the layers in proximity while the cell cultures grow.

Figure 16:
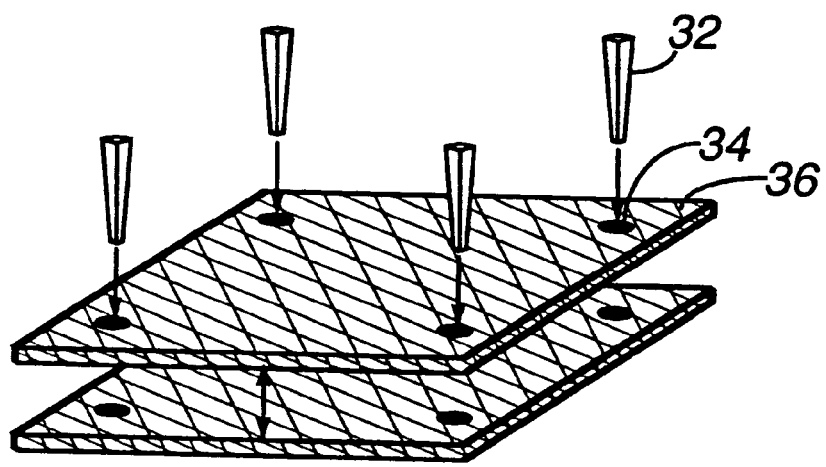
FIG. 16 is a schematic representation of multiple scaffold layers being assembled with pins according to the present invention.

Yet another embodiment of the invention is illustrated in FIG. 16. In this approach, pins 32 are pushed into pre-drilled holes 34 in the scaffold 36. The holes 34 can be slightly undersized to obtain a friction fit. Alternatively, insertion of the pins can be facilitated by using a compliant scaffold material and a rigid pin, by cooling the pins prior to insertion to reduce their diameter, or using split pins (as depicted in the FIG. 16). The outside surface of the pins 32 may be etched to improve friction/gripping properties.

Another preferred embodiment of the invention is illustrated in FIG. 17. In this embodiment, scaffold sections are stacked into prefabricated, biodegradable containers. The individual scaffold sections 40, 42, 44, 46 and 48 are not joined to each other, rather are held in place within the container 50. The container can be porous and/or have inlet/outlet ports to attach vessels to. Similarly, clamps and cable tie-straps can be used to hold and to fix sections together. In the embodiment of FIG. 17, the container 50 includes a biodegradable cap 52, which encloses the container 50 and may use fasteners such as screws 54 or other fasteners described herein to close the container.

In still another strategy, biodegradable or non-biodegradable, non-reactive (e.g., titanium) surgical staples carried in and fired by stapling instruments, such as those manufactured by Ethicon Endo-Surgery, Cincinnati, Ohio, can be used to fasten subsections of scaffolding together.

A surface feature on an individual scaffold segment will become an internal feature when another segment is assembled over it. For example, surface features such as channels can be produced by molding, machining, or by 3D printing (e.g., layer 60 with channels 61 in FIG. 18). Once the next scaffold section (e.g., layer 62 in FIG. 18) is mated with that lower surface, the surface feature becomes an internal scaffold feature. One application is to create an internal matrix of tubules for cell infusion and/or angiogenesis. Another strategy for producing surface features, illustrated in FIG. 19, is to place individual segments of scaffold 66, separated from each other, between layers of scaffold 67, 68, to explicitly form channels.

Figure 20:
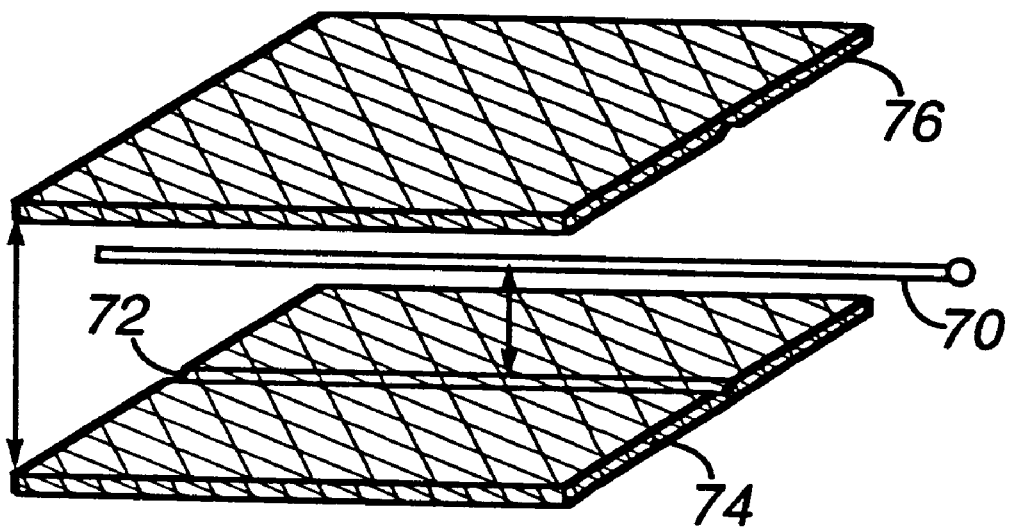
FIG. 20 is a schematic representation of incorporating embedded components, such as vessels, into scaffolds according to the present invention.
Figure 21:
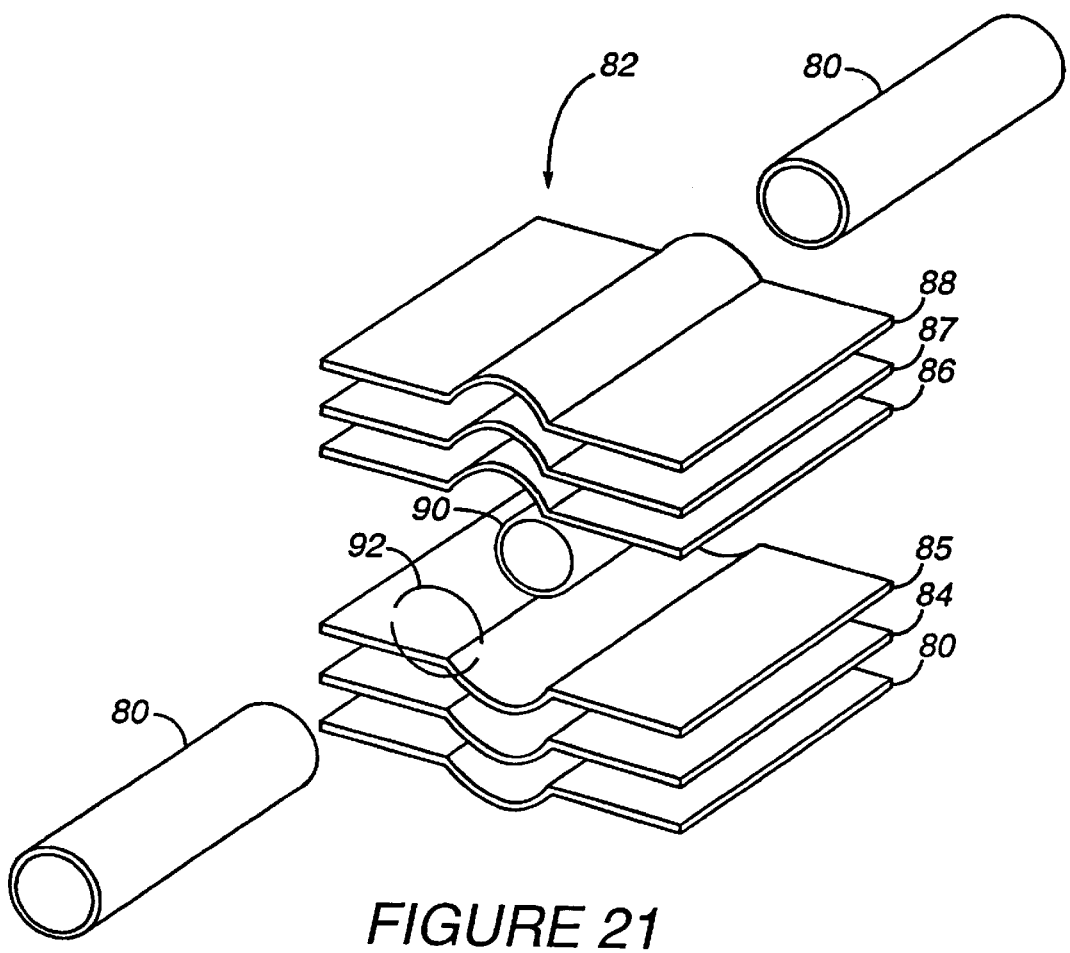
FIG. 21 is an isometric exploded view of a three dimensional, multiple layer scaffold of the present invention, incorporating blood vessels into preformed channels.
Figure 22:
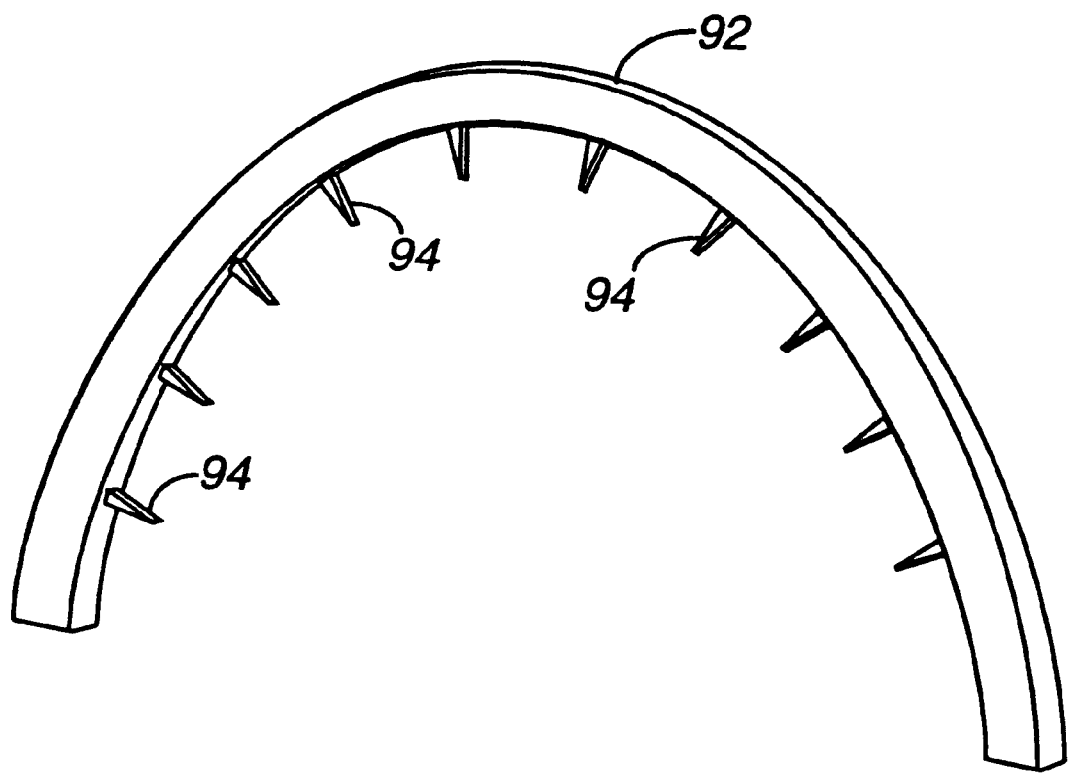
FIG. 22 is an isometric view of a vessel fastener useful in practicing the present invention.

Just as living cells can be impregnated into scaffold sections before assembly, other delicate components can be embedded into the scaffold by assembling sections around these components. For example, as illustrated in FIG. 20, one possibility for creating vasculature is to first place a natural or synthetic vessel 70 into a surface channel 72 of a scaffold section 74. A molding technique for fabricating synthetic collagen-based vessels is, for example, disclosed in Okano and Matsuda, "Hybrid Muscular Tissues: Preparation of Skeletal Muscle-Incorporated Collagen Gels," Cell Transplantation, Vol. 6, No. 2, 109–118 (1997). Then, the vessel becomes embedded within the entire scaffold when the subsequent scaffold section 76 is mated over the other section 74. Yet another opportunity for embedding is to embed an intact vessel during surgery, by assembling the scaffold in-vivo around that vessel. FIG. 21 illustrates the approach for embedding synthetic vessels within three dimensional scaffold material. In this embodiment, an intact, in-vivo blood vessel 80 is sectioned, in order for placement of a three dimensional scaffold generally 82 between the sectioned vessels 80. The scaffold 82 is comprised of multiple subsections 83–88. In the embodiment illustrated in FIG. 21, the subsections 85 and 86 are closest to the synthetic blood vessel 90 which, as illustrated, may have a textured outer surface to assist in retaining the vessel 90 within the scaffold 82. In one embodiment, the synthetic vessel 90 has been placed within the scaffold 82 in a bioreactor prior to implantation. The existing vessels 80 are secured to either end of the synthetic vessel 90 using known microsurgical techniques. The subsections 83–88 of the scaffold 82 have been assembled with fasteners and seeded with cells in the manner previously described. In a highly preferred embodiment, a barbed halo 92, shown in greater detail in FIG. 22, is used to secure the scaffold 82 to the existing vessels 80. This is accomplished, for example, by positioning the halo 92 around the outer surface of the vessel 80 in order to create a "lock washer" for precluding the axial movement of the scaffold 82 with respect to the vessels 80. The halo 92 can be first fastened to the scaffold 82, for example, with solvent or glue, prior to assembling the scaffold 82 around the blood vessel 80. In a preferred embodiment, a barbed halo 92 can be positioned at every juncture of the scaffold 82 with a blood vessel 80. Further support could be provided, for example, by suturing the halo 92 to both the vessel 80 and the synthetic vessel 90 and/or the scaffold 82 using known microsurgical techniques.

As illustrated in FIG. 21, the halo 92 may comprise two semicircular sections. One such section is illustrated in detail in FIG. 22. As illustrated, the halo 92 includes a plurality of barbs which may comprise spike-shaped elements, or may be shaped similar to the single and double-headed barbs illustrated in FIGS. 11 and 12. The halo is preferably fabricated of a biodegradable/biocompatible material, and can be molded.

In general, it is preferred that all of the fasteners described herein be fabricated of biodegradable/biocompatible materials. It is, of course, possible to use non-biodegradable materials, provided they are biocompatible. For example, titanium screws and/or staples can be used as fasteners according to the present invention.

Support structures might be needed for several instances, e.g., for 'unconnected' regions, for supporting steep overhanging features made out of highly compliant materials, and for substrates upon which to start assembling the scaffold. The scaffold sections can be attached to the support structures using the same mating strategies described above. The support sections can be passive and therefore not be seeded with cells. However, during in-vitro and/or in-vivo culturing, cells and fibrous tissue could invade the support structures. Therefore, the microstructure and material composition of support structures is preferably designed to inhibit ingrowth.

Growth factors can, according to the present invention, be incorporated into subsections either with or without cells. For example, according to the present invention, it is possible to provide alternating layers of scaffolding, one layer having been seeded with only cells, the next having been seeded with only growth factors prior to fastening the layers together. Other combinations are, of course, possible. For a general discussion of growth factors and their use see Saltsman, suora. As another example, gradients of growth factor can be achieved in the scaffold of the present invention, for example, by providing layers or subsections of scaffolding, each having homogeneous, but different, concentrations of growth factor relative to adjacent layers or subsections. Further, different types of growth factors can be used in different layers or subsections relative to those used in other layers or subsections.

All of the aforementioned assembly strategies can be automated within a CAD/CAM environment, and all assembly can be done within liquid culture media if required. Additionally, the aforedescribed fasteners may be used in combination, for example, both sutures and screws may be advantageously employed in the same scaffold when fastening scaffold subsections together.

EXAMPLES

Seeding of cells and scaffold preparation were performed in the following manner.

Subsections of hydroxyapatite/polymer scaffold, each approximately 10 mm in diameter and 1 mm thick, were steam sterilized in an autoclave and pre-soaked for 24 hours in a tissue culture medium, such as Dilbecco's Modified Eagle's Medium.

A male New Zealand White Rabbit (Orycytolagus cuniculus) was anesthetized intramuscularly, and positioned in the supine position. The lower abdominal wall, inguinal region, and lateral surfaces of both thighs and legs were shaved, depilated, and prepared for aseptic surgery.

A drill and cutting burr were used to create a small femoral defect. Bone marrow was harvested by injecting several cc's of harvest medium into the medullary canal to displace the marrow.

The harvested bone marrow was mixed with 4 cc of heparinized tissue culture medium in a test tube, and centrifuged for three minutes. Some of the supernatant was discarded to concentrate the cell number, the cell count was checked to verify that the number of cells was greater than $1 \times 10^8$/ml.

Individual subsections of the scaffold material were then soaked in the bone marrow cell suspension by placing the scaffold subsections individually in a test tube containing the cell suspension. The test tube was capped, and a vacuum was created by drawing air out of the test tube with a 10 cc syringe passed through the cap. This vacuum drawing technique speeds and improves diffusion of cells deeply into the scaffold.

When a hydrophilic scaffold material is used, such as hydroxyapatite, it may be useful to pre-soak the scaffold in blood serum in order to improve adherence of the seeded cells to the scaffold.

The individual scaffold subsections were permitted to soak in the suspension of bone marrow cells for several minutes. Two subsections were then sewn together using monofilament nylon sutures as fasteners. The first suture was passed through central region of one disc, and through the central region of a second disc, then brought back through both discs about 1 mm from the first hole to create a button-hole effect. The suture ends were tied and cut short. Four equally spaced sutures were then placed about the perimeter of the discs, tied, and cut short. The sutures were tied to create a snug relationship between adjoining layers of scaffold. The joined scaffold subsections were again immersed in the cell suspension, which was again vacuum drawn. This procedure was repeated until a three dimensional scaffold having five 1 mm thick subsections was seeded with bone marrow cells and stabilized with sutures.

The three-dimensional scaffold was then implanted in the same rabbit from which the bone marrow was harvested, using the rabbit, in effect, as a bioreactor to support growth of bone cells seeded into the scaffold as a result of the bone marrow cell seeding.

The seeded three dimensional scaffold was implanted intramuscularly adjacent and superficial to the deep inferior epigastric right vascular bundle. A control scaffold, also sutured, five layers thick, but unseeded, was implanted in like manner on the left vascular bundle.

The incisions were closed, and the implanted scaffold permitted to support cell growth for at least six weeks. The animals will be monitored at six, eight, and twelve week intervals to assess the degree of tissue generation.

Although the invention has been described in terms of advantages realized and in detail in the foregoing embodiments for the purpose of illustration, it is to be understood that such advantages and detail are solely for illustrative purposes, and that variations can be made therein by those skilled in the art without departing from the spirit and scope of the invention, which is described by the following claims, including all equivalents thereof.

We claim:

1. A three dimensional multilayer scaffold for supporting cell growth comprising:
    a first layer for supporting cell growth; and
    a second layer for supporting cell growth, said first and second layers being mechanically fastened together.

2. The three dimensional multilayer scaffold of claim 1, wherein said first and second layers are mechanically fastened together by a mechanical fastener selected from the group consisting of screws, pins, sutures, staples, wires, string and combinations thereof.

3. The three dimensional multilayer scaffold of claim 2, wherein said mechanical fastener is bioabsorbable.

4. The three dimensional multilayer scaffold of claim 1, wherein said first layer includes a channel.

5. The three dimensional multilayer scaffold of claim 1, wherein each of said layers includes an alignment indentation on one surface thereof and an alignment protrusion on an opposing surface thereof, the alignment indentations shaped to mate with the alignment protrusions for facile alignment of said layers.

6. The three dimensional multilayer scaffold of claim 1, wherein said first layer is seeded with a component selected from the group consisting of living cells, bone marrow cells, osteoblasts, mesenchymal stem cells, satellite cells, fibroblasts, and growth factors.

7. The three dimensional multilayer scaffold of claim 6, wherein said second layer is seeded with a component selected from the group consisting of living cells, bone marrow cells, osteoblasts, mesenchymal stem cells, satellite cells, fibroblasts, and growth factors.

8. The three dimensional multilayer scaffold of claim 1, wherein said first and second layers are subdivided into zones of support for a pre-selected component.

9. The three dimensional multilayer scaffold of claim 8, wherein said zones of support for a pre-selected component define three dimensional heterogeneous regions in the three dimensional multilayer scaffold.

10. The three dimensional multilayer scaffold of claim 1, further including a blood vessel embedded therein.

11. The three dimensional multilayer scaffold of claim 10, further including a barbed halo positioned around said blood vessel's outer surface.

12. A method of forming a three dimensional multilayer scaffold comprising:

seeding a first prefabricated element with a component selected from the group consisting of living cells, bone marrow cells, osteoblasts, mesenchymal stem cells, satellite cells, fibroblasts, and growth factors;

seeding a second prefabricated element with a component selected from the group consisting of living cells, bone marrow cells, osteoblasts, mesenchymal stem cells, satellite cells, fibroblasts, and growth factors; and connecting said first and second prefabricated elements together in a manner that ensures viability of said cellular components.

13. The method of claim 12, wherein a mechanical fastener connects said first and second prefabricated elements.

14. A method of treating a patient comprising:

constructing a three dimensional scaffold to support cell growth, said three dimensional scaffold including a first layer for supporting cell growth, and a second layer for supporting cell growth, said first and second layers being mechanically connected to each other; and implanting said three dimensional scaffold in the patient.

15. The method of claim 14, wherein said first layer is pre-seeded with a cellular component selected from the group consisting of bone marrow cells, osteoblasts, mesenchymal stem cells, satellite cells, fibroblasts, and growth factors.

16. The method of claim 15, wherein said second layer is pre-seeded with a cellular component selected from the group consisting of bone marrow cells, osteoblasts, mesenchymal stem cells, satellite cells, fibroblasts, and growth factors.

17. The method of claim 14, wherein said three dimensional scaffold further includes a plurality of other layers mechanically connected to said first and second layers.

18. The method of claim 14, further including the step of embedding a vessel in said three dimensional scaffold.

19. The method of claim 18, further including the step of connecting the vessel to an existing vessel.

\* \* \* \* \*

UNITED STATES PATENT AND TRADEMARK OFFICE
CERTIFICATE OF CORRECTION

PATENT NO.    : 6,143,293
DATED         : November 7, 2000
INVENTOR(S)   : Weiss et al.

It is certified that error appears in the above-identified patent and that said Letters Patent is hereby corrected as shown below:

Title page,
Item [73], Assignee: after "Carnegie Mellon", add -- University --.

Signed and Sealed this

Eighth Day of October, 2002

Attest:

JAMES E. ROGAN
Attesting Officer
Director of the United States Patent and Trademark Office

UNITED STATES PATENT AND TRADEMARK OFFICE
CERTIFICATE OF CORRECTION

PATENT NO.    : 6,143,293
DATED         : November 7, 2000
INVENTOR(S)   : Weiss et al.

It is certified that error appears in the above-identified patent and that said Letters Patent is hereby corrected as shown below:

Title page,
Item [73], Assignee, after "Carnegie Mellon", add -- University --; and delete "University of Pittsburgh" in its entirety.

Signed and Sealed this

Twenty-eighth Day of December, 2004

JON W. DUDAS
*Director of the United States Patent and Trademark Office*